US008784857B2

(12) United States Patent
Savage

(10) Patent No.: US 8,784,857 B2
(45) Date of Patent: Jul. 22, 2014

(54) ARTICLES INCORPORATING ABSORBENT POLYMER AND CERAGENIN COMPOUND

(75) Inventor: Paul B. Savage, Mapleton, UT (US)

(73) Assignee: Brigham Young University, Provo, UT (US)

(*) Notice: Subject to any disclaimer, the term of this patent is extended or adjusted under 35 U.S.C. 154(b) by 0 days.

(21) Appl. No.: 13/288,902

(22) Filed: Nov. 3, 2011

(65) Prior Publication Data

US 2012/0107382 A1    May 3, 2012

Related U.S. Application Data

(60) Provisional application No. 61/456,204, filed on Nov. 3, 2010.

(51) Int. Cl.
  *A01N 25/04*   (2006.01)
  *A01N 25/08*   (2006.01)
  *A61L 15/20*   (2006.01)
  *A61K 31/575*  (2006.01)
  *A61K 9/70*    (2006.01)
  *B65D 81/26*   (2006.01)

(52) U.S. Cl.
  USPC ........... 424/409; 424/400; 424/443; 426/124; 514/169; 514/182; 604/367

(58) Field of Classification Search
  None
  See application file for complete search history.

(56) References Cited

U.S. PATENT DOCUMENTS

| | | | | |
|---|---|---|---|---|
| 4,842,593 A | * | 6/1989 | Jordan et al. | 604/360 |
| 4,865,855 A | | 9/1989 | Hansen et al. | |
| 2002/0091278 A1 | * | 7/2002 | Savage et al. | 552/9 |

FOREIGN PATENT DOCUMENTS

| | | |
|---|---|---|
| EP | 0341951 | 11/1989 |
| WO | WO 03/090799 | 11/2003 |
| WO | WO 2004/112852 | 12/2004 |
| WO | WO 2007/134176 | 11/2007 |

OTHER PUBLICATIONS

Judy N. Chin, Michael J. Rybak, Chrissy M. Cheung and Paul B. Savage. Antimicrobial Activities of Ceragenins against Clinical Isolates of Resistant *Staphylococcus aureus*. Antimicrobial Agents and Chemotherapy, vol. 51, No. 4, Apr. 2007, p. 1268-1273.*
Paul B. Savage, Jason Nielsen, Xin-Zhong Lai, Yanshn Feng, Yang Li, Gard Nelson, Matthew R. Linford, Carl Genberg. Antibacterial Activities of Thin Films Containing Ceragenins. Microbial Surfaces, Chapter 5, ACS Symposillm Series vol. 984, pp. 65-78. Publication Date: May 30, 2008.*
X Z Lai et al: "Controlled Release of a Bactericidal Ceragenin-Polymer Conjugate", 46th Annual Interscience Conference on Antimicrobial Agents and Chemotherapy, Sep. 27, 2006, pp. 1-1, XP55016796, San Francisco, USA Retrieved from the Internet: URL:http://web.archive.org/web/20070307040930/http://www.ceragenix.com/2.pdf [retrieved on Jan. 18, 2012].
P B Savage et al: "Use of a Ceragenin-Based Coating to Prevent Bacterial Colonization of Urinary Catheters", 48th Annual Interscience Conference on Antimicrobial Agents & Chemotherapy, Oct. 26, 2008, pp. 1-1, XP55016798, Washington DC, USA Retrieved from the Internet: URL:http://n8medical.com/PDF/CatheterCoatingPresentation.pdf [retrieved on Jan. 18, 2012].
P B Savage et al: "Thin Films Containing Ceragenins Prevent Biofilm Formation on Endotracheal Tubes", 9th International Federation of Infection Control Congress, Oct. 14, 2008, pp. 1-1, XP55016800, Santiago, Chile Retrieved from the Internet: URL:http://www.n8medical.com/PDF/EndotrachealTubePoster-IFIC.PDF [retrieved on Jan. 18, 2012].
T R Fritsch et al: "In Vitro Activity of Nine Developmental Cationic Steroid Compounds (Ceragenins) against Clinical Isolates of Clostridium difficile", The 46th Interscience Conference on Antimicrobial Agents and Chemotherapy, Sep. 27, 2006, pp. 1-1, XP55016797, San Francisco, USA Retrieved from the Internet: URL:http://web.archive.org/web/20070307040637/http://www.ceragenix.com/6.pdf[retrieved on Jan. 18, 2012].
Emily L. Perry et al: "Assessing pen-implant tissue infection prevention in a percutaneous model", Journal of Biomedical Materials Research Part B: Applied Biomaterials, vol. 92B, Nov. 19, 2009, pp. 397-408, XP55017067, ISSN: 1552-4973, DOI: 10.1002/jbm.b.31528.
Savage et al: "Antibacterial Activities of Thin films Containing Ceragenins", Microbial Surfaces: Structure, Interactions, and Reactivity, ACS, May 30, 2008, pp. 65-78, XP009155636, DOI: 10.1021/BK-2008-0984.CH005.

* cited by examiner

*Primary Examiner* — Frederick Krass
*Assistant Examiner* — Michael P Cohen
(74) *Attorney, Agent, or Firm* — Workman Nydegger

(57) ABSTRACT

An absorbent article includes an absorbent polymer and a ceragenin compound. The ceragenin compound has a sterol group and a plurality of cationic groups that mimic naturally occurring antimicrobial peptides. The ceragenin compound is associated with the absorbent polymer such that upon absorption of a fluid, the ceragenin compound is incorporated or maintained in the absorbent article.

19 Claims, 6 Drawing Sheets

CSA-37

CSA-41

CSA-42

CSA-43

CSA-44

CSA-45

CSA-47

CSA-49

CSA-50

CSA-51

ARTICLES INCORPORATING ABSORBENT POLYMER AND CERAGENIN COMPOUND

CROSS-REFERENCE TO RELATED APPLICATIONS

This application claims the benefit of U.S. Provisional application 61/456,204 filed Nov. 3, 2010, titled "DIAPER WITH CSA ANTIMICROBIAL ACTIVE SITES", which is incorporated herein by reference in its entirety.

BACKGROUND OF THE INVENTION

1. The Field of the Invention

The present invention relates to the use of ceragenin compounds with articles that incorporate absorbent polymers.

2. The Relevant Technology

A superabsorbent polymer is a polymer that can absorb and retain extremely large amounts of a liquid relative to its own mass. In deionized and distilled water a superabsorbent polymer may absorb 500 times its weight (from 30-60 times its own volume). The ability of a superabsorbent polymer to absorb water depends on the ionic concentration of the aqueous solution being absorbed. Saline solutions are less absorbed than distilled water. For example, a saline solution of 0.9% is absorbed by a superabsorbent polymer on the order of 50 times the polymer's weight.

The total absorbency and swelling capacity are controlled by the type and degree of cross-linkers used to make the polymer. Superabsorbent polymers are commonly made from polymerizing acrylic acid blended with sodium hydroxide in the presence of an initiator to form a poly-acrylic acid sodium salt (sometimes referred to as sodium polyacrylate).

The largest use of superabsorbent polymers is in personal disposable hygiene products, such as baby diapers, adult protective underwear, and sanitary napkins.

BRIEF SUMMARY OF THE INVENTION

The present invention relates to absorbent articles (e.g., diapers, hygiene products, absorbent packaging for food) that include an absorbent polymer and a ceragenin compound associated together with a support structure. Ceragenin compounds are anti-microbial compounds that have cationic groups attached to a sterol backbone. The compounds mimic the three dimensional structure of naturally occurring anti-microbial peptides and provide a natural mechanism of killing microbes.

When water comes into contact with the absorbent article the water dissolves all or a portion of the ceragenin compound. Importantly, the ceragenin compounds are only "activated" in the presence of moisture. Once dissolved in solution, the ceragenin compound can inhibit microbial growth for a sustained period of time (e.g., days, weeks, months or years).

When the ceragenin compound is dissolved into a fluid during use, the fluid is retained in the absorbent polymer, thereby incorporating or maintaining incorporation of the ceragenin compound into the absorbent polymer. However, despite the incorporation of the ceragenin into the absorbent polymer (i.e., via the water), the ceragenin compound remains in fluid contact with microbes in the vicinity of the absorbent polymer. Microbes that migrate into the polymer come into contact with the ceragenin compound and are killed. Alternatively, or in addition, ceragenin molecules can elute out of the absorbent polymer and kill microbes in fluid contact with the absorbent polymer.

The association of the ceragenin compound with the absorbent polymer provides control over the location and/or release of the ceragenin molecule while still effectively killing microbes. The hydrophobicity of the ceragenin can be selected to control the rate and/or extent that the ceragenin compound is retained or released from the absorbent polymer. Matching the hydrophobicity of the absorbent polymer to the ceragenin keeps the ceragenin in the absorbent polymer and creating a mismatch in hydrophobicity causes the ceragenin to be eluted. Thus, elution or retention can be selected. Surprisingly the ceragenin compound can continuously kill microbes at a high rate when the ceragenin is non-covalently attached to the absorbent polymer. Associating the ceragenin compound non-covalently through hydrophobic/hydrophilic interactions allows the controlled retention and/or release of the ceragenin compounds without the inactivation that occurs from covalent tethering.

The ceragenin compound can be incorporated into the absorbent article by (i) incorporating the ceragenin into the absorbent polymer, (ii) intimately mixing the ceragenin with the absorbent polymer (e.g., in dry form), and/or (iii) incorporating the ceragenin compound into a supporting structure of the article (e.g., a fabric sheet) that is in fluid communication with water absorbed by the absorbent polymer during use of the article.

The ceragenin compounds can be incorporated into the absorbent article and remain stable during storage. Stability can be achieved using the absorbent polymer in dry form or selecting ceragenins that are stable in the environment in which the absorbent article is stored. The stability of the ceragenin compound can give the article a shelf life of weeks, months, or even years.

The stability of the ceragenin compounds can also be selected to facilitate manufacturing of the absorbent article. For example, stable ceragenin compounds can be incorporated into an absorbent article at a point during manufacturing prior to the article being exposed to high temperatures that would render other microbial agents ineffective. Thus, the stability of the ceragenin compounds facilitates both the manufacture and use of the ceragenin compounds in absorbent articles.

The absorbent articles can be used in diapers, hygiene products, wound care products (e.g., self adhesive bandages), and packaged foods. In one embodiment the absorbent article may be a disposable infant diapers, feminine hygiene product, a sanitary napkin, a panty liner, a tampon, a product for adult incontinence, a personal care wipe, a household wipe, or the like.

Many ceragenin compounds are relatively inexpensive to make and can therefore be used in disposable products such as diapers and hygiene products. If desired, the ceragenin compounds can also be configured to gradually decompose to nontoxic compounds that won't build up in the environment.

These and other features of the present invention will become more fully apparent from the following description and appended claims, or may be learned by the practice of the invention as set forth hereinafter.

BRIEF DESCRIPTION OF THE DRAWINGS

To further clarify the above and other advantages and features of the present invention, a more particular description of the invention will be rendered by reference to specific embodiments thereof which are illustrated in the appended drawings. It is appreciated that these drawings depict only illustrated embodiments of the invention and are therefore not to be considered limiting of its scope. The invention will be described and explained with additional specificity and detail through the use of the accompanying drawings in which.

DETAILED DESCRIPTION

I. Ceragenins

Ceragenin compounds, also referred to herein as cationic steroidal anti-microbial compounds (CSAs), are synthetically produced small molecule chemical compounds that include a sterol backbone having various charged groups (e.g., amine and cationic groups) attached to the backbone. The backbone can be used to orient the amine or guanidine groups on one face, or plane, of the sterol backbone. For example, a scheme showing a compound having primary amino groups on one face, or plane, of a backbone is shown below in Scheme I:

Scheme I

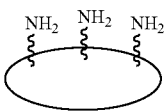

Ceragenins are cationic and amphiphilic, based upon the functional groups attached to the backbone. They are facially amphiphilic with a hydrophobic face and a polycationic face. Without wishing to be bound to any particular theory, the anti-microbial ceragenin compounds described herein act as anti-microbial agents (e.g., anti-bacterials, anti-fungals, and anti-virals). It is believed, for example, that the anti-microbial ceragenin compounds described herein act as anti-bacterials by binding to the outer cellular membrane of bacteria and other microbes and inserting into the cell membrane forming a pore that allows the leakage of ions that are critical to the microbe's survival and leading to the death of the affected microbe. In addition, the anti-microbial ceragenin compound described herein may also act to sensitize bacteria to other antibiotics. For example, at concentrations of the anti-microbial ceragenin compounds below the corresponding minimum bacteriostatic concentration, the ceragenins cause bacteria to become more susceptible to other antibiotics by increasing the permeability of the outer membrane of the bacteria.

The charged groups are responsible for disrupting the bacterial cellular membrane, and without the charged groups, the ceragenin compound cannot disrupt the membrane to cause cell death or sensitization. An example of a ceragenin compound is shown below at Formula I. As will be discussed in greater detail below, the R groups on Formula I can have a variety of different functionalities, thus providing the ceragenin compound with different properties.

Formula I

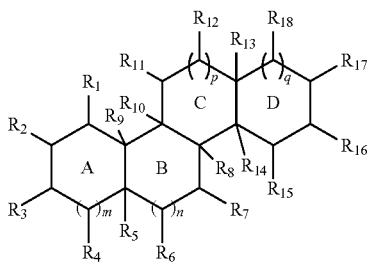

Figure 1:
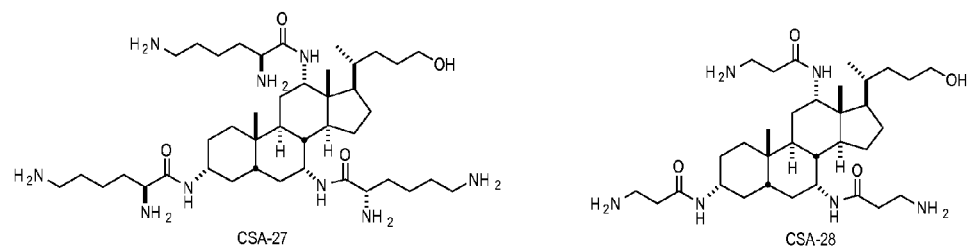
FIG. 1 illustrates example ceragenin compounds.
Figure 1:
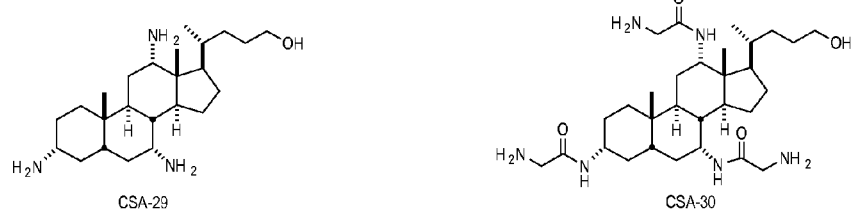
Figure 1:
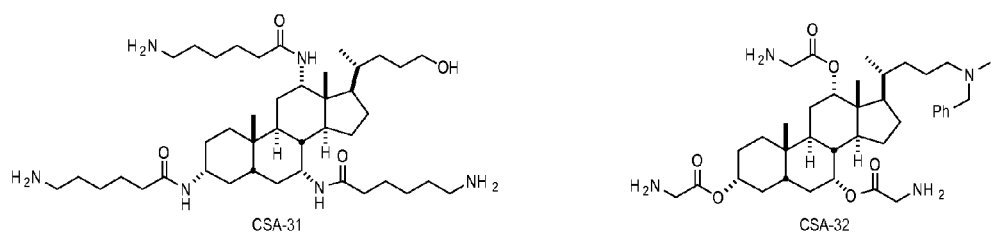
Figure 1:
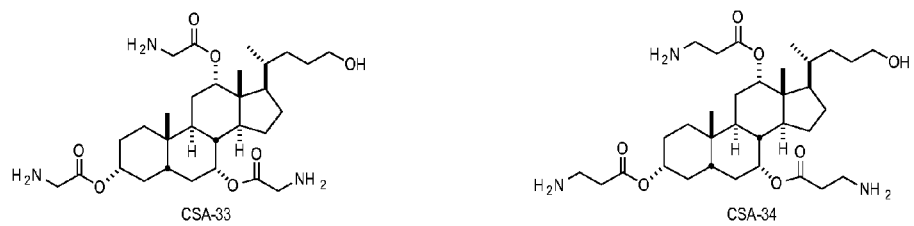
Figure 1:
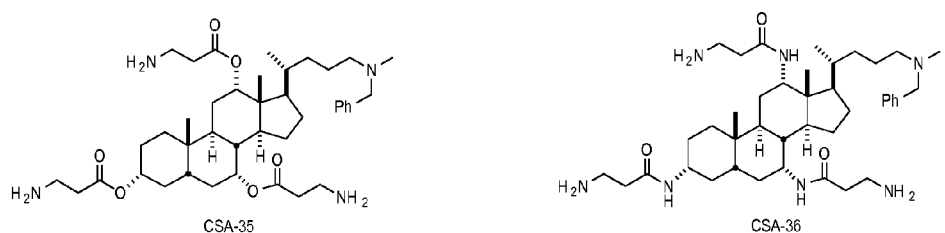
Figure 1:
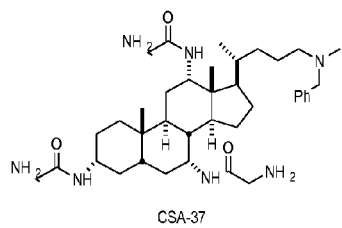
Figure 1:
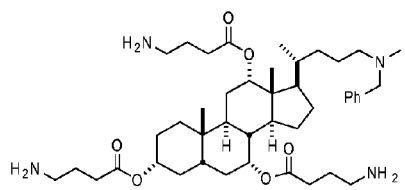
Figure 1:
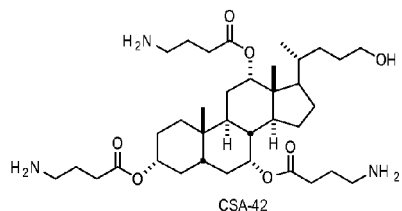
Figure 1:
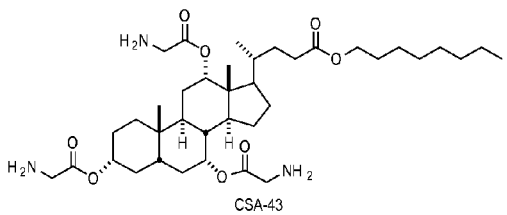
Figure 1:
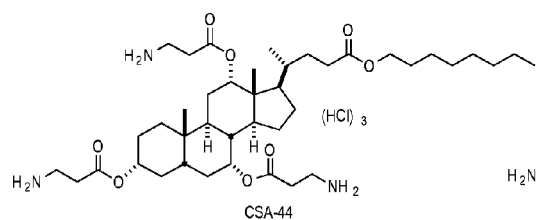
Figure 1:
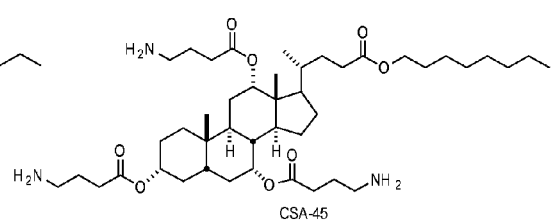
Figure 1:
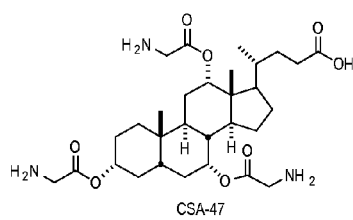
Figure 1:
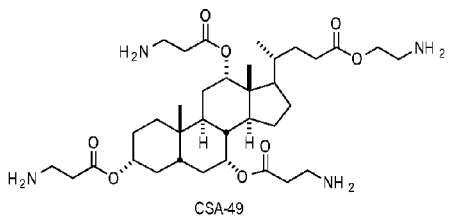
Figure 1:
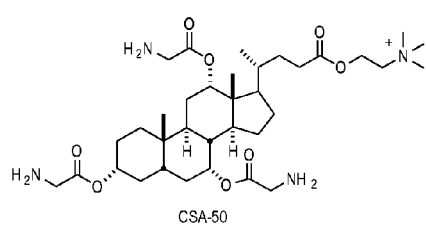
Figure 1:
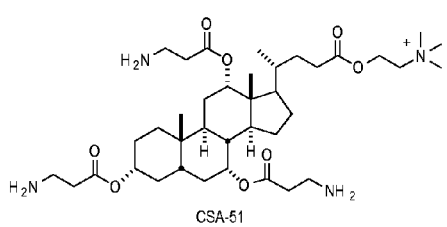
Figure 1:
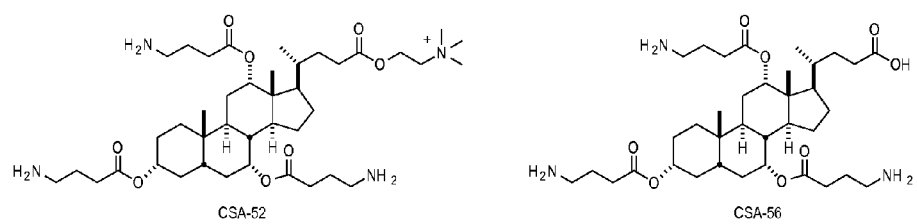
Figure 1:
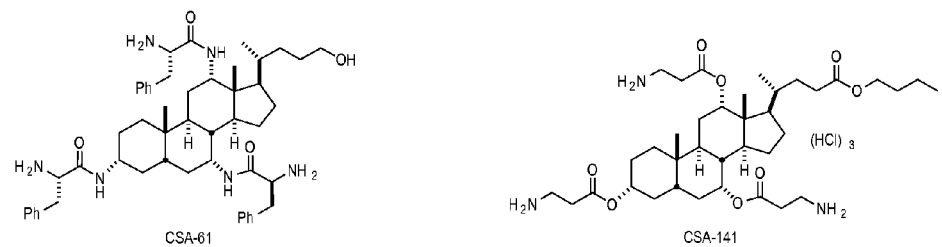
Figure 1:
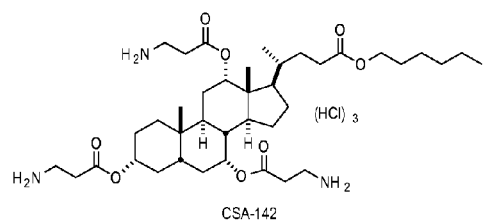

A number of examples of ceragenin compounds having hydrolysable linkages are illustrated in FIG. 1. As explained more fully below, ceragenins with hydrolysable linkages can be advantageous to prevent the ceragenins from persisting beyond a useful period of time.

II. Absorbent Articles

The absorbent articles of the invention include a support structure that incorporates an absorbent polymer and an associated ceragenin compound. The support structure can have any number of layers and/or configuration of layers to provide a support structure into which an absorbent polymer may be incorporated (i.e., deposited on or integrated within). The ceragenin compound is associated with the absorbent polymer in the sense that water absorbed by the polymer will be in fluid contact with the ceragenin compound.

The absorbent articles may have several surfaces. In general, articles may include inner and outer layers that "sandwich" an absorption layer. The inner shell and outer shell layers and the absorption layer can form several surfaces including a body facing surface (on a first outside shell layer), an outer shell layer (on the outside surface opposite the body facing surface), interfacial surfaces between or within the shell layers; surfaces of an absorbent inner layer. In some embodiments, the body facing surface includes a material and/or configuration that wicks fluids away from skin and toward the absorption layer.

The particular material used for a support structure will depend on the absorbent article being manufactured. For example, in the case of a diaper, the material may be a cellulose-containing substrate, such as a moisture absorbent fabric of the type commonly used for diapers. Such fabrics are well known in the art and are preferably used in combination with a super absorbent polymeric material. It is also possible, although less advantageous, to include the ceragemom compounds in conventional cotton or fabrics.

The support structure may include materials that are woven or non-woven. The term "nonwoven" includes spunbond, meltblown, coformed materials, hydroentangled fibers, needle punched or felted nonwovens, wet laid, dry laid fibers, and composites of said fibrous networks. While nonwoven materials are commonly fibrous materials, for the purpose of this disclosure a "nonwoven" may be a foam material, except as specified. For the purpose of describing the diaper or absorbent article, it is described as having three basic layers. In various embodiments of the invention, the three basic layers are not necessarily discrete; and one basic layer may blend with another, or one basic layer may serve the purpose of another by varying the composition or density of the components. For example, in FIG. 2, the outer shell 14 may be a highly densified outer portion of absorbent pad 12.

The layers of the support structure may be bonded together using adhesives, ultrasonic bonding, heating, stitching, and similar methods. In some embodiments of the invention, portions of layers or entire layers are left unbonded. Furthermore, absorbent articles may include fasteners, elastic elements, and containment flaps to facilitate proper fit and avoid leakage.

The support structure includes at least one absorbent polymer that can absorb water or other fluid capable of dissolving the ceragenin compound. In a preferred embodiment, the absorbent polymer includes a superabsorbent polymer. The superabsorbent polymer may have a composition and configuration that causes it to absorb a substantially larger amount of fluid relative to its own mass. (e.g., sodium polyacrylates). Alternatively, or in addition, the absorbent polymer may include natural polymers such as cotton, cellulose, and cellulose derivatives. Also included are synthetic polymers such as viscose rayon, polypropylene, polyethylene, nylon, polyacrylates, polyesters, and polyurethanes or any blends or mixtures of above.

The present invention can be incorporated into any article that includes an absorbent polymer and is typically used in a non-sterile environment. The absorbent article may be a personal hygiene device including a disposable infant diaper, a feminine hygiene product, a sanitary napkin, a panty liner, a tampon, a product for adult incontinence, or the like. The article may be a personal care wipe or a household wipe, or the like. In addition, the article may be an absorbable pad used in health care to maintain a barrier between a surface and the bodily fluids of a patient (e.g., a Chux underpad).

The absorbent article may also be a food grade absorption pad packaged with a food product such as, but not limited to fruit (e.g., berries) or meat (e.g., whole meat poultry, fish, pork, or beef) vegetables, and/or dairy products. Foods packaged with the absorbing articles described herein can reduce spoilage and disease caused by microbes that contaminate food. Surprisingly, even where ceragenins elute too slowly to properly kill a microbial population, by placing the microbes in fluid contact with the absorbent polymer, microbes have been found to migrate into the polymer and be killed, which increases the safety of using the ceragenins in close proximity to food products.

III. Non-Covalent Incorporation of Ceragenins into a Polymer

Ceragenin compounds incorporated into the absorbent polymer can be non-covalently associated with the polymer. Upon contact with moisture, the CSA can leach or elute from the polymer. CSAs are generally soluble in water, and CSAs can be associated with polymers to control release rates. Selection of appropriate polymer and CSA structures allows for an extended period of release of the CSA.

For example, the chain extending from the amine at C17 carbon (Formula I) can be tailored to allow varied rates of elution from the absorbent polymer. Exemplary chains included, lipids, hydrophic chains (e.g., aliphatic), hydrophilic (e.g., polyethyleneoxide), or any chain that interacts with the polymer is a way that allows modification of the rate of elution. Longer chain lengths will retain the CSA within the polymer matrix (in particular the hydrophobic domains). Suitable CSA examples include those compounds illustrated in FIG. 1. Those labeled CSA-13, CSA-92, CSA-102, and CSA-113. CSA-102 with a siloxane group can provide a means of covalent incorporation into silicone polymers. CSA-113 with an acrylamide group can provide a means of covalent incorporation into acrylic-based polymers, including superabsorbents. CSA-92 with a long hydrophobic tail ($C_{16}H_{33}$) can be compatible with polyolefins, or copolymerized with olefins.

The particular CSAs incorporated into the absorbent polymer may be soluble or partially soluble in aqueous solutions. Additionally, CSAs when blended with the water and the appropriate surfactant can be handled in the form of gels, or emulsions. Block copolymers based on ethylene oxide and/or propylene oxide, in particular, Pluronic™-type surfactants, are especially useful for this purpose. Pluronic™ is a product of BASF, a business with offices in Port Arthur, Tex., USA.

IV. Non-Covalent Incorporation During Diaper Assembly or Manufacture

Ceragenin compounds can be incorporated into the diaper at any suitable step during manufacture. For example, in an embodiment, the super-absorbent polymer, or the fluff pulp, or both, can be brought into contact with a solution of ceragenins by immersion, spraying, printing, or coating, etc; the solvent is separated from the treated polymeric material by soaking, evaporation, or centrifugation, etc. If necessary the polymeric materials and absorbent materials are then dried by utilizing forced hot air, oven drying, air at room temperature, microwave drying, or the use of heated drying drums, vacuum chambers, etc. In some manufacturing systems the normal air flow and temperature sufficiently dry the substrate without a discrete drying process.

In a typical disposable diaper making process a bale or roll of dense cellulose pulp is "opened" or "fiberized" to achieve a soft, absorbent fluff pulp. Commonly, water is sprayed into the fluff pulp reduce static charge. In certain embodiments of the invention, a ceragenin suspension or solution replaces or augments the water spray, thereby incorporating the ceragenin into the fluff pulp. If desired, the ceragenin spray can be pulsed or zoned so that certain regions of the absorbent pad can have more ceragenin than other areas.

In other embodiments, the ceragenin can be incorporated into an absorbent pad or other device during its manufacture. For example, with respect to FIG. 2, absorbent pad 12 can be formed on a movable conveyor belt that passes through a "forming chamber." where pressurized nozzles spray onto the conveyor surface absorbent polymer particles (e.g., superabsorbent polymer, fluff pulp) in a solution or suspension that contains ceragenins. The bottom of the conveyor may be perforated, and as the pad material may be sprayed onto the belt. A vacuum may be applied from below so that the fibers are pulled down to form a flat pad. Alternatively, a solution containing ceragenin is sprayed onto the top of the flat pad after it is formed.

A further alternative involves the application of ceragenin solutions or suspensions to an absorbent article as the article itself is assembled or manufactured; this facilitates applying the ceragenin in specified zones on the article. For example, for a diaper it may be desired to apply the ceragenin towards the front 23 or towards the rear 21 of the diaper; and the CSA solution or suspension can be sprayed or printed in the desired region of the diaper.

V. Non-Covalent Incorporation in Nonwoven Material

Figure 2:
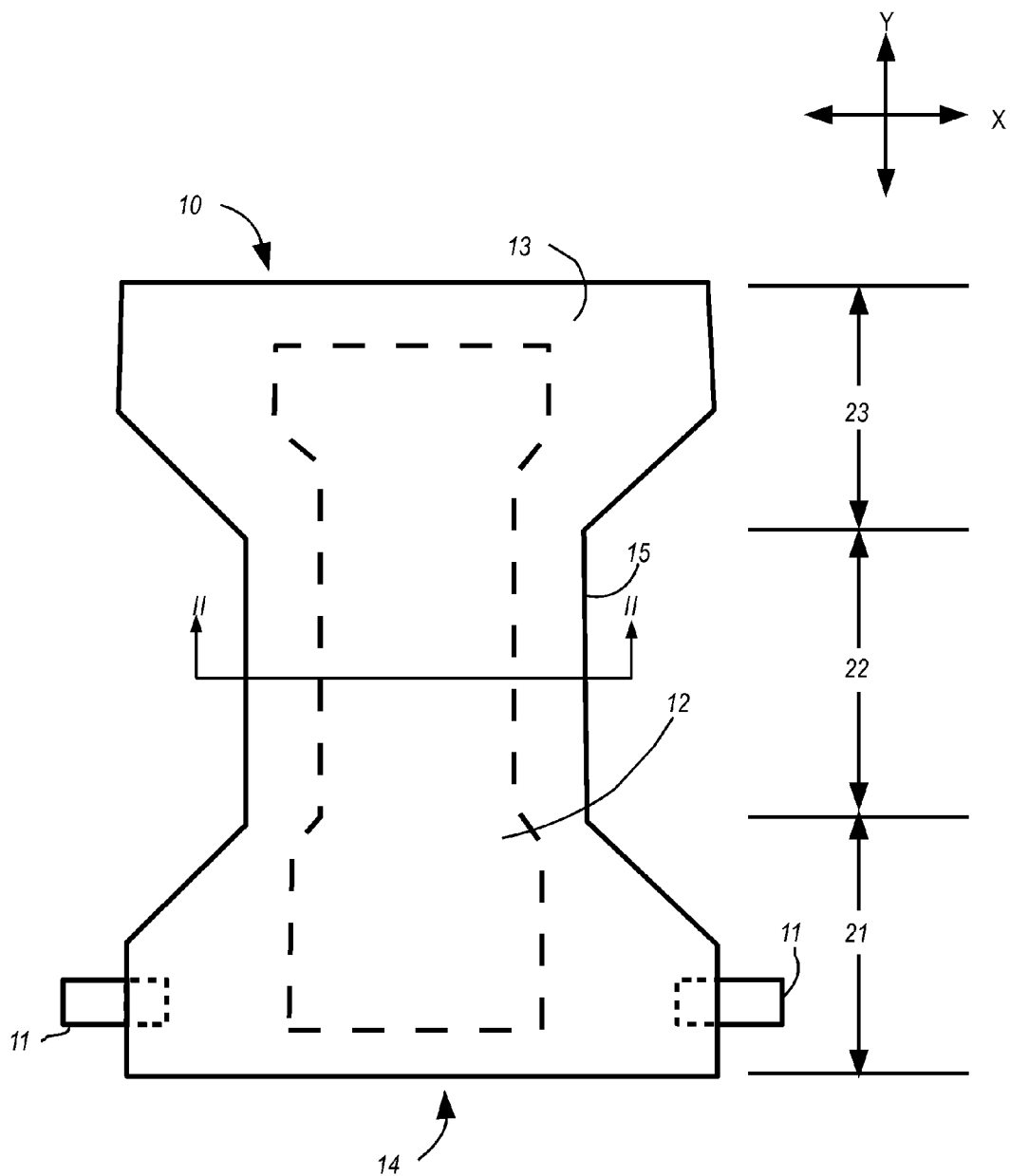
FIG. 2 shows a diaper of the present invention in plan view.

Nonwovens and films are used in various parts of absorbent articles such as diapers. With reference to FIG. 2, inner layer 13 of diaper 10 typically comprises a nonwoven or foraminous film. The term "absorbent fabric" encompasses nonwoven or foraminous films that are intended to absorb liquid. There are several ways to apply a ceragenin to an absorbent fabric, for example, ceragenin compounds may be incorporated into the absorbent fabric in conventional fashion, such as by passage of an absorbent fabric from a supply roll, into a pad bath containing an appropriate concentration of the CSA in solution, through a nip roll to remove excess liquid, and into a dryer to dry the fabric at temperatures adequate to remove excess water.

As another example, ceragenin compounds can be incorporated by passage of a nonwoven web or film through a bath of antimicrobial in a water or water/glycerine bath, the concentration of the antimicrobial being such as to provide the desired effective amount thereof. If necessary, the impregnated fabric is then subjected to drying by passage through a dryer, typically through a stack of steam cans maintained at a suitable temperature that drying of the fabric may occur at any temperature at which the CSA compounds are stable, and which will evaporate any water or alcohol in the solution. For example for CSA-13, the temperature can be in a range from 80-120° C.

The dry, finished absorbent fabric is then prepared for conversion into an absorbent product; it is rolled, cut to size, and stored, wrapped in plastic bags or the like.

Ceragenin compounds are known to be soluble in water. Alternatively, ceragenin compounds are also soluble in such materials as ethanol (and other alcohols), propylene glycol, glycerine, and polyols, or mixtures thereof with or without water can be used in incorporate compounds into the absorbent material. Furthermore ceragenins can be applied as gels, emulsions, suspensions, and in dry form.

VI. Non-Covalent Incorporation into Super-Absorbent Material

In another embodiment ceragenin is incorporated into an absorbent polymer during its formation. Superabsorbent polymers can commonly be made from the polymerization of acrylic acid blended with sodium hydroxide in the presence of an initiator to form a polyacrylic acid sodium salt (sometimes referred to as sodium polyacrylate). Other materials are also used to make a superabsorbent polymer, such as, for example, polyacrylamide copolymer, ethylene maleic anhydride copolymer, cross-linked carboxymethylcellulose, polyvinyl alcohol copolymers, cross-linked polyethylene oxide, and starch grafted copolymer of polyacrylonitrile. Exemplary processes for forming super-absorbent polymers include suspension polymerization and solution polymerization. In suspension polymerization the water based reactant is suspended in a hydrocarbon based solvent. The solution process uses a water based monomer solution to produce a mass of reactant polymerized gel.

In these processes, the ceragenin can be included in the monomer blend during superabsorbent manufacture. The ceragenin in final polymer can be noncovalently incorporated into the polymer and will accordingly elute when contacted with water. Ceragenins with polymerizable groups, such as the acrylamido group on CSA-113 can copolymerize with the acrylic acid monomer, which results in a result in a CSA covalently-bonded to the polymer.

A CSA solution, gel, emulsion, dry powder, or suspension may be applied to the superabsorbent polymer as a spray. The CSA-containing spray can be applied while the superabsorbent is fluidized in an air stream, as the superabsorbent is being blended with fluff pulp, or in the already blended superabsorbent/fluff. Depending upon the quantity of solvent or suspending agent used, a drying step may be required.

VII. Covalent Incorporation of CSAs

As mentioned above, CSAs with polymerizable groups can be covalently bonded to the polymer by incorporating it into the monomer mix. Ceragenins can also be immobilized or permanently attached to a substrate surface, while retaining activity of the ceragenins. This can be accomplishing by direct bonding of a ceragenin to the surface, or by means of an adhesion layer, a coupling agent, or tether.

In addition, the ceragenins can have polymerizable groups, such as the acrylamido group on CSA-113, or an olefin group with an active site that can be copolymerized into the polymer.

VIII. Incorporation of CSA on the Surface of the Inner Layer

Nonwoven materials, such as, for example, nylon, polyester, polyethylene, or polypropylene manufactured by mechanically, chemically, or thermally, heat melting, interlocking the plastic fibers.

In an embodiment, the ceragenin compounds can be incorporated into the one or more of the layers of an article with are mixed with monomers that are used for an inner layer. The monomers are then reacted and polymerized or cured to form a polymer with the ceragenin associated with or covalently bonded to the polymer. The ceragenin used can be modified or unmodified or a conjugate of the ceragenin and another compound to facilitate formation of a slow eluting material.

In an alternative embodiment, the CSA is added to molten polymer prior to the polymer being formed as a film or nonwoven. For example, CSA-92 is dissolved in propylene glycol and added to a molten polypropylene near the end of an extruder, just prior to the polypropylene being formed into a spunbond nonwoven. Given the limited compatibility of the CSA with the polymer, the CSA will tend to migrate towards the surface as the fibers are being drawn.

A polyolefin-based inner layer nonwoven or film, as manufactured, may lack suitable sites to anchor CSA. Methods of priming the polyolefin, such as flame treatment, corona treatment, plasma treatment, and acid washes are known in the art to facilitate printing and adhesive bonding to polyolefins. Such methods can also be used to facilitate bonding the CSA to the inner layer. The priming treatment is advantageously done shortly before the CSA is added to the nonwoven or film.

Suitable CSA compounds for use in the inner layer can be, for example, conjugates of any of the monomers or other compounds that function as monomers, conjugates with modifiers, conjugates with selected solubility properties, or unconjugated CSAs. The CSA compounds can be applied by any suitable method, such as contacting the film with a suitable solution of a CSA compound that coats or associates with the surface. Certain polymer compositions used for inner layers may contain reactive sites that are available for direct attachment or attachment through a coupling agent or a tether (e.g., PEG). In addition, CSA compounds can be incorporated through a conjugate that is attached, solubilized, or otherwise incorporated into the inner layer.

IX. Stabilization of Ceragenins by pH

In one embodiment a ceragenin compound can have hydrolysable linkages that attach the cationic groups to the sterol group (e.g., ester bonds). Hydrolysis of these linkages inactivates the ceragenin. To make the ceragenin stable, an acid can be added to achieve a pH less than 6, 5.5, 5, or 4.5 and optionally greater than 2, 2.5, or 3 or a range thereof. Stability before use is important to give a desired shelf life and instability during and after use can be desirable to prevent long term accumulation of ceragenins in biological systems.

Examples, of ceragenins that include hydrolysable linkages includes, but is not limited to suitable ceragenin compounds that can be used in this embodiment, include but are not limited to, CSA-32, CSA-33, CSA-34, CSA-35, CSA-41, CSA-42, CSA-43, CSA-44, CSA-45, CSA-47, CSA-49, CSA-50, CSA-51, CSA-52, CSA-56, CSA-141, CSA-142. The acid can be a fluid or a solid. (e.g., acetic acid or citric acid, respectively) and can be blended with a superabsorbent/pulp blend.

As discussed above, it may be advantageous to adjust the degree of neutralization of the superabsorbent polymer to improve the stability of the ceragenin. The degree of neutralization of the superabsorbent polymer can be adjusted during its manufacturing process, or subsequently. Alternatively, the ceragenin can be suspended or dissolved in an acidic solution; and when the ceragenin suspension or solution is added to the superabsorbent the degree of neutralization of the superabsorbent would thereby be adjusted.

In any of the embodiments where ceragenin sites are incorporated into the absorbent polymer, or attached to a polymer surface, acidic sites may be optionally provided to stabilize the ceragenin active sites, and extend the duration of the antimicrobial effect. Cellulose materials, which are common in diaper absorbents, have numerous sites, particularly —OH sites, to which acidic functional groups can be added, such as, for example, carboxy groups (or moieties with carboxy groups or acidic groups). In a similar manner, the polymer materials used in the inner layer may have reactive sites for attachment of acidic functional groups. For non-cellulosic polymers, carboxy or other acidic groups can be added in a similar manner.

Many superabsorbent polymers for use in diapers are partially neutralized, crosslinked, acrylic acid-based polymers. The degree of neutralization of the polymer correlates to the carboxylic acid (R—COOH) versus carboxylate (R—COO—X+) ratio. The degree of neutralization of the superabsorbent polymer can be adjusted to provide sufficient acidic sites for the ceragenins. This can increase the duration of the antimicrobial activities during storage, particularly in a moist or humid environment, and also during use of the article. Alternatively, acid sites can be provided by infiltrating the absorbent or nonwoven polymer with an acidic substance, which is retained or elutes sufficiently slow to maintain an acidic environment.

The acidity of the absorbent can be measured using any suitable method. As an example, a saturating solution of the polymer can be tested or the whole absorbent article can be tested.

X. Diapers

Figure 3:
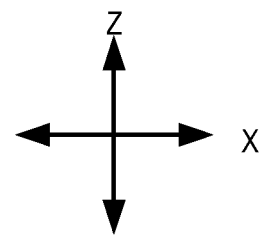
FIG. 3 shows the diaper of FIG. 2 in cross section taken along line II-II.
Figure 3:
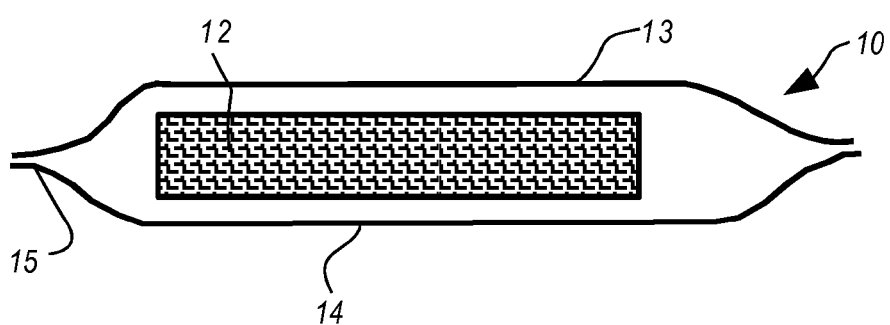

A diaper is generally depicted in FIGS. 2 and 3; the diaper 10 includes three basic layers: (i) an outer shell 14; (ii) an absorbent pad 12; and (iii) an inner layer 13. The diaper also includes a perimeter region 15, a front region 23, a crotch portion 22, and a rear portion 21. Fasteners 11 are disposed on the rear portion 21. The outer shell 14 typically comprises a film and/or nonwoven fabric. An important function of the outer shell 14 is to retain liquid and soil in the diaper. The outer shell 14 may permit transpiration of water vapor, i.e., it may be breathable, and help provide a drier environment within the diaper.

The absorbent pad 12 absorbs, distributes, and retains body fluids. The absorbent pad 12 commonly comprises a blend of superabsorbent polymers and fluff pulp. In other embodiments the absorbent pad 12 may comprise tissue layers, synthetic polymer fibers, nonwoven fibers, odor absorbents, color indicators, and adhesives. The absorbent pad 12 may be a homogeneous layer, or it may comprise multiple layers. The composition and/or density of the absorbent may vary in the x, y, or z directions.

The absorbent pad 12 may include strips, or zones, or pockets of different composition or density than adjacent portions of the absorbent pad 12. A common component of the absorbent pad is fluff pulp, i.e., fluffed cellulose pulp, typically made from wood, especially softwood. Such absorbent fluff pulp is commercially available in bale or roll form. In some embodiments of the invention the absorbent pad 12 includes 0-99% fluff pulp. In other embodiments of the invention the absorbent pad 12 includes 1-100% superabsorbent polymer. In further embodiments of the invention, the absorbent pad 12 comprises 15-60% superabsorbent polymer and 40-85% fluff pulp.

Alternatively or additionally, the absorbent pad may contain synthetic absorbent cellulose fibers, such as rayon. Synthetic fibers, such as polyesters and polyolefins, may also be used to good effect. In some embodiments the absorbent fibers are treated with surfactant agents. The inner layer 13 separates the wearer of the diaper from the absorbent pad 12. The inner layer 13 absorbs fluid and transfers the fluid to the absorbent pad 12. As such, the inner layer 13 is fluid permeable. The inner layer 13 comprises a first layer, which may comprise a film or nonwoven. In various configurations the first layer is foraminous, and/or may be treated to modify its hydrophilic/hydrophobic balance. Optionally, the inner layer 13 further comprises an acquisition layer, i.e., a layer that is configured to rapidly intake and distribute fluid. The acquisition layer is typically a nonwoven material is positioned adjacent the first layer of the inner layer 13. The inner layer has a body-contacting surface, and a reverse surface, (not shown) the reverse surface facing towards the adjacent absorbent pad.

The absorbent pad 12 in diapers is specially designed to absorb, distribute and retain body fluids. The inner layer 13, separates the wearer from the absorbent pad 12, facilitates rapid intake of fluid and provides a comfortable surface that contacts the wearer. The outer shell 14 functions as a barrier to liquid helps prevent leakage. Diapers are frequently made by a multi-step process in which the absorbent pad 12 is formed, then attached to an inner layer 12, and an outer shell 14 as a continuous "sausage". The layers may be trimmed using a water jet, die cut, or other means. Optionally elastics, fasteners 11, and barrier cuffs may also be added to the diaper. The inner layer 12 and the outer shell 14 are sealed together along their perimeter 15 by application of heat, adhesives, or ultrasonic vibrations. The continuous sausage is cut into separate diapers, and the diapers are packaged.

Figure 4:
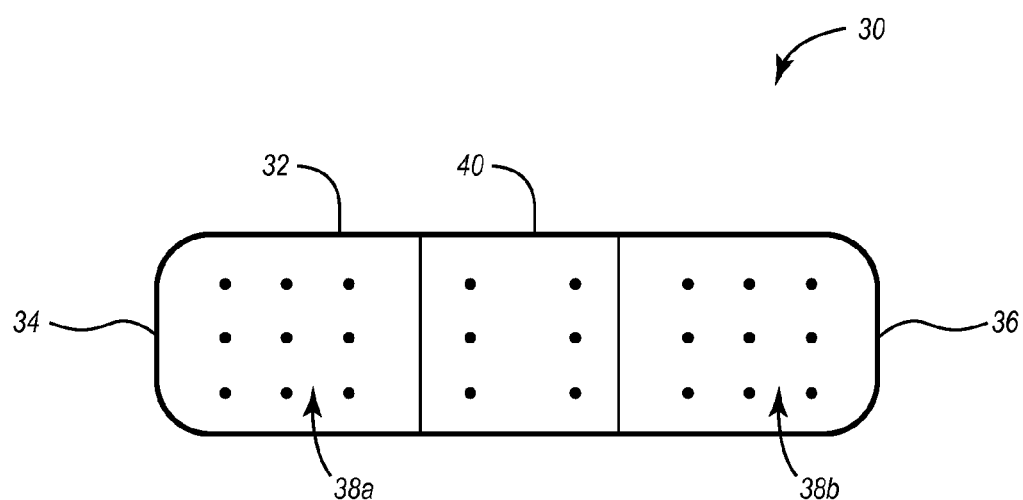
FIG. 4 illustrates an adhesive bandage.

FIG. 4 illustrates a bandage 30 that can be used in wound care. Bandage 30 includes an elongate strip 32 of a flexible material that extends from a first end 34 to a second end 36. Strip 32 includes a plurality of perforations that allow the bandage to breath. Outer sections 34a and 34b have a biocompatible adhesive that allows the bandage to be attached to a person's skin. Center portion 40 includes a gauze adsorbent and/or a super adsorbent polymer and a ceragenin compound. Ceragenin compounds can optionally be applied to outer sections 34a and 34b or an upper surface if desired. Those skilled in the art will recognize that bandage 30 can have a different shape or size according to sizes and shapes known in the art. In addition, ceragenins can be associated with adsorbents for other wound care products such as, but not limited to gauze and wrapping.

XI. Function of CSA in an Absorbent Article

The primary function of a personal absorbent product is to absorb body fluids and prevent leakage. In the process of absorbing body fluids it is desired that the fluid the products absorb does not become a haven or breeding medium for microorganisms. Additionally, in the warm, moist environment microorganisms on the wearer's skin can proliferate. CSA, properly disposed in an absorbent article can restrict the growth of such microorganisms.

Microorganisms, and bacteria in particular, are undesirable because they catalyze the breakdown of substances in the urine, creating products that cause a strong odor and skin irritation, by limiting microbial growth CSA can limit such problems.

Additionally microorganisms are thought to have a role in the development of diaper dermatitis, "yeast" infections, and toxic shock syndrome (TSS). TSS, is associated with proliferation *Staphylococcus aureus* bacteria; and it is expected that appropriate use of CSA will reduce the likelihood of such events.

The concentration of CSA associated the absorbent article is dependent upon the particular CSA compounds and absorbent composition. The concentration, in general, should be at least the minimum inhibitory concentration (MIC) of the CSA, at or near the surface of the absorbent material. MIC is defined the lowest concentration of an antimicrobial that will inhibit the visible growth of a microorganism after overnight incubation. This is a well documented and accepted diagnostic test. The MIC of the particular CSA can be determined, and its properties with the absorbent matched to produce at least an MIC concentration for the target bacteria at or near the surface of the absorbent. Examples of MIC values for certain CSA compounds can be found at C. Li, et al. "*Anti-* microbial Activities of Amine- and Guanidine-Functionalized Cholic Acid Derivatives" Antimicrobial Agents and Chemotherapy, Vol. 43, No. 6, June 1999, p. 1347-1349.

XII. Ceragenin Compounds

The ceragenin compound may have a structure as shown in Formula I:

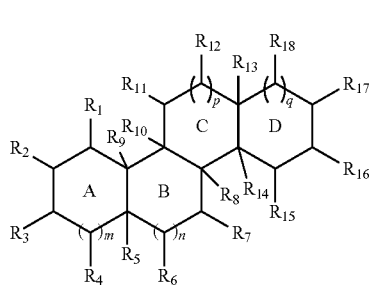

Formula I where each of fused rings A, B, C, and D is independently saturated, or is fully or partially unsaturated, provided that at least two of A, B, C, and D are saturated, wherein rings A, B, C, and D form a ring system; each of m, n, p, and q is independently 0 or 1; each of $R_1$ through $R_4$, $R_6$, $R_7$, $R_{11}$, $R_{12}$, $R_{15}$, $R_{16}$, $R_{17}$, and $R_{18}$ is independently selected from the group consisting of hydrogen, hydroxyl, a substituted or unsubstituted $(C_1-C_{10})$alkyl, $(C_1-C_{10})$hydroxyalkyl, $(C_1-C_{10})$alkyloxy-$(C_1-C_{10})$alkyl, $(C_1-C_{10})$alkylcarboxy-$(C_1-C_{10})$alkyl, $(C_1-C_{10})$alkylamino-$(C_1-C_{10})$alkyl, $(C_1-C_{10})$alkylamino-$(C_1-C_{10})$alkylamino, $(C_1-C_{10})$alkylamino-$(C_1-C_{10})$alkylamino-$(C_1-C_{10})$alkylamino, a substituted or unsubstituted $(C_1-C_{10})$ aminoalkyl, a substituted or unsubstituted aryl, a substituted or unsubstituted arylamino-$(C_1-C_{10})$alkyl, $(C_1-C_{10})$haloalkyl, $C_2-C_6$ alkenyl, $C_2-C_6$ alkynyl, oxo, a linking group attached to a second steroid, a substituted or unsubstituted $(C_1-C_{10})$aminoalkyloxy, a substituted or unsubstituted $(C_1-C_{10})$aminoalkyloxy-$(C_1-C_{10})$alkyl, a substituted or unsubstituted $(C_1-C_{10})$aminoalkylcarboxy, a substituted or unsubstituted $(C_1-C_{10})$aminoalkylaminocarbonyl, a substituted or unsubstituted $(C_1-C_{10})$aminoalkylcarboxamido, $H_2N-HC(Q_5)-C(O)-O-$, $H_2N-HC(Q_5)-C(O)-N(H)-$, $(C_1-C_{10})$azidoalkyloxy, $(C_1-C_{10})$cyanoalkyloxy, P.G.-HN-HC$(Q_5)$-C(O)-O-, $(C_1-C_{10})$guanidinoalkyloxy, $(C_1-C_{10})$quaternaryammoniumalkylcarboxy, and $(C_1-C_{10})$guanidinoalkyl carboxy, where $Q_5$ is a side chain of any amino acid (including a side chain of glycine, i.e., H), P.G. is an amino protecting group, and each of $R_5$, $R_8$, $R_9$, $R_{10}$, $R_{13}$, and $R_{14}$ is independently deleted when one of fused rings A, B, C, or D is unsaturated so as to complete the valency of the carbon atom at that site, or selected from the group consisting of hydrogen, hydroxyl, a substituted or unsubstituted $(C_1-C_{10})$alkyl, $(C_1-C_{10})$hydroxyalkyl, $(C_1-C_{10})$alkyloxy-$(C_1-C_{10})$alkyl, a substituted or unsubstituted $(C_1-C_{10})$aminoalkyl, a substituted or unsubstituted aryl, $(C_1-C_{10})$haloalkyl, $C_2-C_6$ alkenyl, $C_2-C_6$ alkynyl, oxo, a linking group attached to a second steroid, a substituted or unsubstituted $(C_1-C_{10})$aminoalkyloxy, a substituted or unsubstituted $(C_1-C_{10})$aminoalkylcarboxy, a substituted or unsubstituted $(C_1-C_{10})$aminoalkylaminocarbonyl, $H_2N-HC(Q_5)-C(O)-O-$, $H_2N-HC(Q_5)-C(O)-N(H)-$, $(C_1-C_{10})$azidoalkyloxy, $(C_1-C_{10})$cyanoalkyloxy, P.G.-HN-HC$(Q_5)$-C(O)-O-, $(C_1-C_{10})$guanidinoalkyloxy, and $(C_1-C_{10})$guanidinoalkylcarboxy, where $Q_5$ is a side chain of any amino acid, PG. is an amino protecting group, provided that at least two or three of $R_{1-4}$, $R_6$, $R_7$, $R_{11}$, $R_{12}$, $R_{15}$, $R_{16}$, $R_{17}$, and $R_{18}$ are independently selected from the group consisting of a substituted or unsubstituted $(C_1-C_{10})$aminoalkyl, a substituted or unsubstituted $(C_1-C_{10})$aminoalkyloxy, $(C_1-C_{10})$alkylcarboxy-$(C_1-C_{10})$alkyl, $(C_1-C_{10})$alkylamino-$(C_1-C_{10})$alkylamino, $(C_1-C_{10})$alkylamino-$(C_1-C_{10})$alkylamino-$(C_1-C_{10})$alkylamino, a substituted or unsubstituted $(C_1-C_{10})$aminoalkylcarboxy, a substituted or unsubstituted arylamino$(C_1-C_{10})$alkyl, a substituted or unsubstituted $(C_1-C_{10})$aminoalkyloxy-$(C_1-C_{10})$aminoalkylaminocarbonyl, a substituted or unsubstituted $(C_1-C_{10})$aminoalkylaminocarbonyl, a substituted or unsubstituted $(C_1-C_5)$aminoalkylcarboxyamido, a $(C_1-C_{10})$quaternaryammonium alkylcarboxy, $H_2N-HC(Q_5)-C(O)-O-$, $H_2N-HC(Q_5)-C(O)-N(H)-$, $(C_1-C_{10})$azidoalkyloxy, $(C_1-C_{10})$cyanoalkyloxy, P.G.-HN-HC$(Q_5)$-C(O)-O-, $(C_1-C_{10})$guanidinoalkyloxy, and a $(C_1-C_{10})$guanidinoalkylcarboxy; or a pharmaceutically acceptable salt thereof.

In Formula I, at least two or three of $R_3$, $R_7$, or $R_{12}$ may independently include a cationic moiety attached to the Formula I structure via a hydrolysable linkage. Optionally, a tail moiety may be attached to Formula I at $R_{17}$. The tail moiety may be charged, uncharged, polar, non-polar, hydrophobic, amphipathic, and the like. Although not required, at least two or three of m, n, p. and q are 1. In a preferred embodiment, m, n, and p=1 and q=0.

A "ring" as used herein can be heterocyclic or carbocyclic. The term "saturated" used herein refers to the fused ring of Formula I having each atom in the fused ring either hydrogenated or substituted such that the valency of each atom is filled. The term "unsaturated" used herein refers to the fused ring of Formula I where the valency of each atom of the fused ring may not be filled with hydrogen or other substituents. For example, adjacent carbon atoms in the fused ring can be doubly bound to each other. Unsaturation can also include deleting at least one of the following pairs and completing the valency of the ring carbon atoms at these deleted positions with a double bond; such as $R_5$ and $R_9$; $R_8$ and $R_{10}$; and $R_{13}$ and $R_{14}$.

The term "unsubstituted" used herein refers to a moiety having each atom hydrogenated such that the valency of each atom is filled.

The term "halo" used herein refers to a halogen atom such as fluorine, chlorine, bromine, or iodine.

Examples of amino acid side chains include but are not limited to H (glycine), methyl (alanine), —CH$_2$—(C=O)—NH$_2$ (asparagine), —CH$_2$—SH (cysteine), and —CH(OH)—CH$_3$ (threonine).

An alkyl group is a branched or unbranched hydrocarbon that may be substituted or unsubstituted. Examples of branched alkyl groups include isopropyl, sec-butyl, isobutyl, tert-butyl, sec-pentyl, isopentyl, tert-pentyl, isohexyl. Substituted alkyl groups may have one, two, three or more substituents, which may be the same or different, each replacing a hydrogen atom. Substituents are halogen (e.g., F, Cl, Br, and I), hydroxyl, protected hydroxyl, amino, protected amino, carboxy, protected carboxy, cyano, methylsulfonylamino, alkoxy, acyloxy, nitro, and lower haloalkyl.

The term "substituted" used herein refers to moieties having one, two, three or more substituents, which may be the same or different, each replacing a hydrogen atom. Examples of substituents include but are not limited to halogen (e.g., F, Cl, Br, and I), hydroxyl, protected hydroxyl, amino, protected amino, carboxy, protected carboxy, cyano, methylsulfonylamino, alkoxy, alkyl, aryl, aralkyl, acyloxy, nitro, and lower haloalkyl.

An aryl group is a $C_{6-20}$ aromatic ring, wherein the ring is made of carbon atoms (e.g., $C_6$-$C_{14}$, $C_{6-10}$ aryl groups).

Examples of haloalkyl include fluoromethyl, dichloromethyl, trifluoromethyl, 1,1-difluoroethyl, and 2,2-dibromoethyl.

An aralkyl group is a group containing 6-20 carbon atoms that has at least one aryl ring and at least one alkyl or alkylene chain connected to that ring. An example of an aralkyl group is a benzyl group.

A linking group is any divalent moiety used to link one compound to another. For example, a linking group may link a second compound to a compound of Formula I. An example of a linking group is $(C_1-C_{10})$alkyloxy-$(C_1-C_{10})$alkyl.

Amino-protecting groups are known to those skilled in the art. In general, the species of protecting group is not critical, provided that it is stable to the conditions of any subsequent reaction(s) on other positions of the compound and can be removed at the appropriate point without adversely affecting the remainder of the molecule. In addition, a protecting group may be substituted for another after substantive synthetic transformations are complete. Clearly, where a compound differs from a compound disclosed herein only in that one or more protecting groups of the disclosed compound has been substituted with a different protecting group, that compound is within the disclosure. Further examples and conditions are found in T. W. Greene, *Protective Groups in Organic Chemistry*, (1st ed., 1981, 2nd ed., 1991).

A person of skill will recognize that various ceragenin compounds described herein preserve certain stereochemical and electronic characteristics found in steroids. The term "single face," as used herein, refers to substituents on the fused sterol backbone having the same stereochemical orientation such that they project from one side of the molecule. For example, substituents bound at $R_3$, $R_7$ and $R_{12}$ of Formula I may be all β-substituted or α-substituted. The configuration of the moieties $R_3$, $R_7$ and $R_{12}$ may be important for interaction with the cellular membrane.

Compounds include but are not limited to compounds having cationic groups (e.g., amine or guanidine groups) covalently attached to a steroid backbone or scaffold at any carbon position, e.g., cholic acid. In various embodiments, a group is covalently attached at anyone, or more, of positions $R_3$, $R_7$, and $R_{12}$ of the sterol backbone. In additional embodiments, a group is absent from anyone, or more, of positions $R_3$, $R_7$, and $R_{12}$ of the sterol backbone.

Anti-microbial CSA compounds described herein may also include a tether or "tail moiety" attached to the sterol backbone. The tail moiety may have variable chain length or size and may be one of charged, uncharged, polar, non-polar, hydrophobic, amphipathic, and the like. In various embodiments, a tail moiety may be attached at $R_{17}$ of Formula I. A tail moiety may include the heteroatom (O or N) covalently coupled to the sterol backbone. The tail moiety may, for example, be configured to alter the hydrophobicity/hydrophilicity of the ceragenin compound. Ceragenin compounds of the present disclosure having different degrees of hydrophobicity/hydrophilicity may, for example, have different rates of uptake into different target microbes. Likewise, altering the hydrophobicity/hydrophilicity of the ceragenin compounds described herein may affect the retention of the ceragenin compounds in certain media.

Other ring systems can also be used, e.g., 5-member fused rings. Compounds with backbones having a combination of 5- and 6-membered rings are also contemplated. Cationic functional groups (e.g., amine or guanidine groups) can be separated from the backbone by at least one, two, three, four or more atoms.

The present invention may be embodied in other specific forms without departing from its spirit or essential characteristics. The described embodiments are to be considered in all respects only as illustrative and not restrictive. The scope of the invention is, therefore, indicated by the appended claims rather than by the foregoing description. All changes which come within the meaning and range of equivalency of the claims are to be embraced within their scope.

What is claimed is:

1. An absorbent article, comprising:
a support structure; and
an absorbent polymer and a ceragenin compound associated with one another and supported on the support structure, the ceragenin compound including a sterol group and a plurality of cationic groups attached thereto;
wherein the ceragenin compound and absorbent polymer are a dry blended mixture or the ceragenin compound is provided at a pH between 2 and 6; and
wherein the ceragenin compound includes hydrolysable linkages between the sterol group and at least a portion of the cationic groups such that the ceragenin compound can degrade by hydrolysis in water.

2. The absorbent article of claim 1, wherein the ceragenin compound is non-covalently attached to the absorbent polymer so as to associate the ceragenin compound with the absorbent polymer but allow the ceragenin compound to be released from the polymer in the presence of a microbe.

3. The absorbent article of claim 1, wherein the ceragenin compound and the absorbent polymer are a dry blended mixture.

4. The absorbent article of claim 1 wherein the ceragenin compound is associated with the absorbent polymer such that upon exposure to an aqueous environment, the ceragenin compound elutes from the absorbent polymer in sufficient amount to provide an antimicrobial effect.

5. The absorbent article of claim 1, wherein the support structure includes at least one sheet of a material.

6. The absorbent article of claim 5, wherein the at least one sheet of material includes a nonwoven fabric, wherein the ceragenin compound is in or on the surface of the nonwoven fabric.

7. The absorbent article of claim 1, further comprising material comprising cellulosic fibers.

8. The absorbent article of claim 1, wherein the ceragenin is water hydrolysable ceragenin selected from the group consisting of CSA-32, CSA-33, CSA-34, CSA-35, CSA-41, CSA-42, CSA-43, CSA-44, CSA-45, CSA-47, CSA-49, CSA-50, CSA-51, CSA-52, CSA-56, CSA-141, CSA-142, and combinations thereof.

9. The absorbent article of claim 1, further comprising an acidic material covalently or non-covalently associated with the absorbent polymer.

10. The absorbent article of claim 1 wherein the absorbent polymer comprises a polyacrylate-based superabsorbent polymer, with carboxylic acid groups (R—COOH) and carboxylate salts (R—COO-M+), and a mole ratio of carboxylic acid groups to carboxylate salts that is greater than 1:1.

11. The absorbent article of claim 1 wherein the amount of ceragenin compound associated with the support structure is sufficient to provide at least a minimum inhibitory concentration (MIC) for the ceragenin compound at or near an article-contacting body surface of the article.

12. The absorbent article of claim 11 wherein the type and concentration of the ceragenin compound is selected to provide an MIC sufficient to inhibit the growth of *Staphylococcus aureus* type MRSA or VRSA.

13. The absorbent article of claim 1 wherein the ceragenin compound is covalently bonded on a surface of the absorbent article.

14. The absorbent article of claim 1, wherein the absorbent article is a disposable diaper, a feminine hygiene product, a sanitary napkin, a panty liner, a tampon, a product for adult incontinence, a personal care wipe, or a household wipe.

15. The absorbent article of claim 1, wherein the article is a diaper and the support structure includes an outer shell, an absorbent pad, and an inner layer, wherein the absorbent pad includes absorbent polymer and the inner layer includes a material that wicks moisture toward the absorbent pad.

16. The absorbent article of claim 15, wherein the ceragenin compound is disposed on an upper surface of the inner layer opposite the absorbent pad and/or within or on the absorbent pad.

17. The absorbent article of claim 1, wherein the article is a bandage, the support structure comprising a flexible strip and the absorbent polymer disposed on the flexible strip, the flexible strip further comprising an adhesive that attaches the bandage to skin.

18. A packaged food comprising, a food material and an absorbent as in claim 1.

19. A packaged food as in claim 18, wherein the food material is a fruit, a vegetable, a dairy, a pork, a fish, a poultry, or a beef product or a combination thereof.

* * * * *

UNITED STATES PATENT AND TRADEMARK OFFICE
CERTIFICATE OF CORRECTION

PATENT NO. : 8,784,857 B2  Page 1 of 1
APPLICATION NO. : 13/288902
DATED : July 22, 2014
INVENTOR(S) : Savage It is certified that error appears in the above-identified patent and that said Letters Patent is hereby corrected as shown below:

In the Specification

Column 7
Line 5, change "used in incorporate" to --used to incorporate--
Line 51, change "with are" to --which are--

Column 10
Line 24, change "34a and 34b" to --38a and 38b--
Line 29, change "34a and 34b" to --38a and 38b--

Signed and Sealed this
Twenty-third Day of June, 2015

Michelle K. Lee
*Director of the United States Patent and Trademark Office*